United States Patent [19]

Seeger et al.

[11] 4,094,977
[45] June 13, 1978

[54] COMBINATION PREPARATION OF ESTROGEN AND PROSTAGLANDIN

[75] Inventors: Karl Seeger, Hofheim, Taunus; Fritz Bauer, Bad Soden am Taunus, both of Germany

[73] Assignee: Hoechst Aktiengesellschaft, Frankfurt am Main, Germany

[21] Appl. No.: 699,262

[22] Filed: Jun. 24, 1976

[30] Foreign Application Priority Data

Jun. 26, 1975  Germany ............................ 2528419

[51] Int. Cl.$^2$ .................. A61K 31/56; A61K 31/215; A61K 31/19
[52] U.S. Cl. .................................... 424/240; 424/305; 424/317; 424/346
[58] Field of Search .................. 424/240, 305, 317

[56] References Cited

PUBLICATIONS

Saksena et al., - Fertility and Sterility, vol. 26, No. 2, (1975), pp. 126–130.
Ham et al., - Chem. Abst. vol. 83, (1975), p. 22664k.
Pike et al., - Prostaglandin Bibliography (1968), pp. 53 and 60, (Ramwell et al. and Hawkins et al.).

*Primary Examiner*—Sam Rosen
*Attorney, Agent, or Firm*—Curtis, Morris & Safford

[57] ABSTRACT

A pharmaceutical combination preparation which comprises as active substances at least one compound selected from the group of the luteolytically effective prostaglandins or derivatives thereof and at least one compound selected from the group of the estrogenic substances, in a weight ratio of from 1:1 to 1:5,000, in admixture with the usual adjuvants and/or carrier material.

8 Claims, No Drawings

COMBINATION PREPARATION OF ESTROGEN AND PROSTAGLANDIN

The present invention relates to a combination preparation of estrogen and prostaglandin.

It is known that prostaglandins, especially those of the $F_2\alpha$-series, play an important part in the reproduction cycle of mammals, although the nature of the physiological activity has not yet been elucidated (L. Speroff, P. W. Ramwell, Am. J. Obstetr., Gynecol. 107, (1970), 1111–30; J. R. Weeks, Ann. Rev. Pharmacol. 12 (1972), 317–336). Derivatives of prostaglandins of the $F_2\alpha$-series have been especially disclosed to possess luteolytic activity and to be suitable for initiating and synchronizing estrus in commercially reared animals (for example, horses, cattle, pigs and sheep) (Prostaglandins 6, (1974), 87).

It is also known that estrogens have a luteolytic effect under very definite conditions.

An abortive effect of a combination of a depot $F_2\alpha$-prostaglandin with depot estradiol in rats has also been reported (S. K. Saksena et al., Fertility and Sterility 26, No. 2 (1975), 126–130).

It has now been found that a combination of a luteolytically effective prostaglandin, especially a compound of the series of the $F_2\alpha$-prostaglandins, on the one hand, and a compound of a group of the estrogenic compounds, on the other hand, produces a substantially increased luteolytic effect in mammals, especially an estrogeneous effect in commercially reared animals, and an obstetric effect in women. The increased effect obtained is of synergistic nature, i.e. it is superior to one obtained by simply adding the effects of the two substances.

The compounds to be used according to the invention are selected from the group of the luteolytically effective prostaglandins, for example the $F_2\alpha$-prostaglandins of the formula I

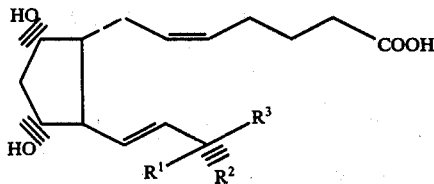

in which $R^1$ and $R^2$, which are different from each other, each stands for hydrogen or a hydroxy group, but $R^1$ especially stands for hydrogen and $R^2$ for a hydroxy group, and $R^3$ stands for 1.1 an n-pentyl radical or 1.2 an n-hexyl radical carrying a straight-chain alkyl group of 1 to 4 carbon atoms attached to one of the carbon atoms numbered 1 to 5 of the hexyl group or a methyl, ethyl, methylene, ethylidene or vinyl radical or a methyl radical and a methylene radical, or two methyl radicals attached to the sixth carbon atom of the n-hexyl radical (see, German Offenlegungsschrift No. 2,150,361).

2. the radical X—O—R, wherein X and R have the following meaning:

2.1 X stands for a straight chain or branched chain alkylene group of 1 to 5 carbon atoms, and R stands for a saturated or unsaturated, straight chain or branched chain hydrocarbon radical of 1 to 8 carbon atoms, a straight chain or branched chain oxo-alkyl group of 2 to 8 carbon atoms, and the ethylene glycol or ethylene thioglycol acetal thereof, a straight chain or branched chain hydroxyalkyl group of 2 to 8 carbon atoms, the hydroxy group being in terminal position, or for a straight chain or branched chain carboxyalkyl group of 2 to 8 carbon atoms (see German Ofenlegungsschrift No. 2,416,193), or 2.2 X stands for a straight chain or branched chain alkyl group of 1 to 5 carbon atoms, or a phenyl or benzyl group which may carry, on its nucleus, one to three halogen atoms, trifluoromethyl, hydroxy, alkyl and/or alkoxy groups, each having 1 to 4 carbon atoms, and R stands, if X is a straight chain or branched chain alkyl group of 1 to 5 carbon atoms, for a diphenyl ether group which may either be unsubstituted or carry, on one or both nuclei, one to three halogen atoms, trifluoromethyl, hydroxy, alkyl and/or alkoxy groups, each of 1 to 4 carbon atoms, or for an unsubstituted phenoxyalkyl group or a phenoxyalkyl group which carries, on its nucleus, one to three halogen atoms, trifluoromethyl, hydroxy, alkyl and/or alkoxy groups, each of 1 to 4 carbon atoms, and in which the alkyl moiety is of straight chain and contains 2 to 5 carbon atoms or of branched chain and contains 3 to 6 carbon atoms, or if X is a substituted or unsubstituted phenyl group, for a benzyl group which may carry, on the nucleus, from one to three halogen atoms, trifluoromethyl, hydroxy, alkyl and/or alkoxy groups, each of 1 to 4 carbon atoms, or if X is a substituted or unsubstituted benzyl group, for a phenyl group which may carry, on its nucleus, from one to three halogen atoms, trifluoromethyl, hydroxy, alkyl and/or alkoxy groups, each of 1 to 4 carbon atoms, (see, Belgian Pat. No. 836,950 = German Patent Application No. P 24 16 193.1), or 2.3 X stands for a straight chain or branched chain alkylidene or alkylene group of 1 to 7 carbon atoms or a straight chain or branched chain alkoxy-alkylene group of 2 to 8 carbon atoms, and R stands for an $\alpha$- or $\beta$-thienyl group or an $\alpha$- or $\beta$-thienyl-methyl group, which may both carry, on their nuclei, from one to three halogen atoms, trifluoromethyl, and/or alkyl or alkoxy groups, each of 1 to 6 carbon atoms, and/or a phenyl group which may either be unsubstituted or which carry from one to three halogen atoms, trifluoromethyl and/or alkyl or alkoxy groups, each of 1 to 5 carbon atoms, a benzo[b]thiophene radical which may carry from one to three trifluoromethyl groups, a cyclopentano[b]thiophene radical or cyclohexano[b]thiophene radical (see German Patent Application No. P 25 24 955.2), or 2.4 X stands for an alkylene radical of 1 to 3 carbon atoms, which may be unsubstituted or may carry one or two alkyl group of 1 to 3 carbon atoms, and R stands for an aryl, benzyl or furfuryl radical which is unsubstituted or may carry, in its alkyl moieties, one to three halogen atoms or hydroxy, nitro, phenyl, alkyl, alkenyl, haloalkyl, alkoxy, alkenyloxy or acylamino groups of 1 to 4 carbon atoms or dialkylamino group of 1 to 3 carbon atoms and in which the second, third or fourth carbon atom has no or one alkyl group of 1 to 4 carbon atoms (see German Offenlegungsschrift No. 2,223,365), or 3. $R^3$ stands for the —$CH_2$—$CH_2$—$C_6H_5$ group, in which the phenyl group carries one to three fluorine or chlorine atoms or methyl groups (see B. J. Magerlein et al., Prostaglandins 9, (1975), No. 1, page 5).

Particularly preferred, as compounds to be used according to this invention, are those which have the absolute stereo-isomeric nature of natural prostaglandins $F_2\alpha$, i.e. compounds of formula I, in which $R^1$ stands for hydrogen, and $R^2$ for a hydroxy group.

Among the compounds cited sub 1.1, suitable compounds of formula I are those in which $R^3$ stands for the n-heptyl, n-octyl, 1-methylhexyl, 2-methylhexyl, 3-methylhexyl, 4-methylhexyl, 5-methylhexyl or 6-heptenyl group.

Especially mentioned are, for example, the following compunds:

9α, 11α, 15-trihydroxy-20-ethyl-5-cis,13-trans prostadienic acid,
9α, 11α, 15-trihydroxy-20-vinyl-5-cis,13-trans prostadienic acid,
9α,11α,15 trihydroxy-19,20-dimethyl-5-cis,13-trans-prostadienic acid,
9α,11α,15-trihydroxy-18,20-dimethyl-5-cis,13-trans-prostadienic acid,
9α,11α,15-trihydroxy-16,20-dimethyl-5-cis,13-trans-prostadienic acid, and preferably the corresponding 15α-epimers.

Among the compounds cited sub 2.1, those of formula I are preferred in which R stands for a straight chain or branched chain alkyl group of 1 to 4 carbon atoms, the allyl group, a straight chain or branched chain oxo-alkyl group of 2 to 5 carbon atoms having a terminal oxo group, preferably the 3-oxopropyl or 2-dimethyl-3-oxopropyl group, as well as the oximes and oxime ethers thereof, a straight chain or branched chain hydroxyalkyl group of 2 to 5 carbon atoms, preferably the 2-dimethyl-3-hydroxypropyl group, a straight chain or branched chain carboxyalkyl group of 2 to 5 carbon atoms, preferably the 2-carboxyethyl or 2-dimethyl-2-carboxyethyl group.

Of this group, for example the following compounds are especially recommended for this invention:

9α,11α,15-trihydroxy-16,16-dimethyl-18-oxa-5-cis,13-trans-prostadienic acid,
9α,11α,15-trihydroxy-16,16-dimethyl-18-oxa-5-cis,13-trans-20-nor-prostadienic acid,
9α,11α,15-trihydroxy-16,16,20,20-tetramethyl-18-oxa-5-cis,13-trans-prostadienic acid,
9α,11α,15-trihydroxy-16,19,19-trimethyl-17-oxa-5-cis,13-trans-prostadienic acid, and
9α,11α,15-trihydroxy-16,16-dimethyl-18-oxa-5-cis,13-trans-20-homo-prostadienic acid, preferably the corresponding 15α-epimers.

Among the compounds cited sub 2.2 of formula I, those are preferred in which X stands for the methylene, ethylidene or an isopropylene or isobutylene group or the unsubstituted phenyl or benzyl group, and R is defined as follows: a diphenyl ether group which carries, on one or both phenyl groups, from one to three halogen atoms, especially chlorine atoms and/or alkoxy or alkyl groups of 1 to 3 carbon atoms, especially the methoxy or methyl groups; phenyl, benzyl and the phenoxyalkyl groups of 2 to 4 carbon atoms in the straight chain alkyl moiety, which may carry, on its nucleus, from one to three halogen atoms, especially chlorine atoms, and/or alkoxy or alkyl groups of 1 to 3 carbon atoms, especially methoxy or methyl groups, very preferably one chlorine atom and/or one methoxy group.

In particular, the following compounds of formula I may be used, in which R is defined as follows:
3-chloro-4-(4-chlorophenoxy)phenyl, 4-(4-chlorophenoxy)phenyl, 3-methoxy-4-(4-chlorophenoxy)-phenyl, 3-chloro-4(3-methoxy-4-chlorophenoxy)-phenyl, 2-(3-chlorophenoxy)-ethyl, 2-(3-chlorophenoxy)-propyl, 3-chlorophenyl, 4-chlorophenyl and 3-chloro-4-methoxyphenyl.

Of this group, for example the following compounds are especially mentioned for this invention:

9α,11α,15-trihydroxy-16 methyl-15-(3-chloro-4-(4-chlorophenoxy)phenoxy)-5-cis,13-trans-tetranor-prostadienic acid,
9α,11α,15-trihydroxy-16,16-dimethyl-16-(4-(4-chlorophenoxy)-phenoxy)-5-cis,13-trans-tetranor-prostadienic acid,
9α,11α,15-trihydroxy-16-(4-(4-chlorophenoxy)-phenoxy)-5-cis,13-trans-tetranor-prostadienic acid,
9α,11α,15-trihydroxy-16-(3-methoxy-4-(4-chlorophenoxy)-phenoxy)-5-cis,13-trans-tetranor-prostadienic acid,
9α,11α,15-trihydroxy-16-methyl-16-(2-(3-chlorophenoxy)-ethoxy)-5-cis,13-trans-tetranor-prostadienic acid,
9α,11α,15-trihydroxy-16-(2-(3-chlorophenoxy)-propoxy)-5-cis,13-trans-tetranor-prostadienic acid,
9α,11α,15-trihydroxy-16,16-dimethyl-16-(3-chloro-4-(3-methoxy-4-chlorophenoxy)-phenoxy)-5-cis, 13-trans-tetranor-prostadienic acid,
9α,11α15-trihydroxy-16-(2-(3-chlorophenoxy)-ethoxy)-5-cis,13-trans-tetranor-prostadienic acid,
9α,11α,15-trihydroxy-15-(4-(3-chlorophenoxymethyl)-phenyl)-5-cis,13-trans-pentanor-prostadienic acid,
9α,11α,15-trihydroxy-15-(4-(4-chlorophenoxymethyl)-phenyl)-5-cis,13-trans-pentanor-prostadienic acid,
9α,11α,15-trihydroxy-15-(4-(benzyloxy)-phenyl)-5-cis,13-trans-pentanor-prostadienic acid,
9α,11α,15-trihydroxy-15-(4-(3-chlorobenzyloxy)-phenyl)-5-cis,13-trans-pentanor-prostadienic acid,
9α,11α,15-trihydroxy-15-((4-(4-methylbenzyloxy)-phenyl)-5-cis,13-trans-pentanor-prostadienic acid,
9α,11α,15-trihydroxy-15-(3-chloro-4-(benzoyloxy)-phenyl)-5-cis,13-trans-pentanor-prostadienic acid,
9α,11α,15-trihydroxy-16-(2-(3,4,5-trichlorophenoxy)-ethoxy)-5-cis,13-trans-tetranor-prostadienic acid,
9α,11α,15-trihydroxy-16-(2-(2,4-dichloro-3-methylphenoxy)ethoxy)-5-cis,13-trans-tetranor-prostadienic acid,
9α,11α,15-trihydroxy-16-(2-(2,4-dibromo-3-methylphenoxy)ethoxy)-5-cis,13-trans-tetranor-prostadienic acid, and
9α,11α,15-trihydroxy-16,16-dimethyl-16-(3-methoxy-4-(2,4-dichlorophenoxy)-phenoxy)-5-cis,13-trans-tetranor-prostadienic acid, preferably the corresponding 15α -epimers.

Among the compounds of formula I cited sub 2.3, there are suitable those in which X stands for the methylene, ethylidene, isopropylene, isobutylene or methoxyethylene group, and R is defined as follows:
an unsubstituted α- or β-thienyl group or an α- or β-thienylmethyl group, and α- or β-thienyl and thienylmethyl group which are substituted by one to three chlorine atoms, trifluoromethyl and/or methoxy or methyl groups, or for a phenyl group which is unsubstituted or carries from 1 to 3 halogen atoms, especially chlorine atoms, trifluoromethyl and/or alkoxy or alkyl groups of 1 to 3 carbon atoms, especially the methoxy or methyl groups. Preferably substituents of $R^3$ are the benzo[b]-thienyl, cyclopentano[b]thienyl and cyclohexano[b]thienyl groups which may be unsubstituted or carry from one to three trifluoromethyl groups.

Particularly preferred are compounds of the invention in which R is defined as follows:

3-thienyl, 2-(2'-methyl)-thienyl, 2-(3-methoxy)-thienyl, 2-(3-methoxy)-thienylmethyl, 3-(2-ethoxymethyl)-thienyl, 3-(2-methoxymethyl)-thienyl, 2-(3-chloro)-thienyl, 2-(2-thienyloxy)ethyl, 3-(2',3'-dimethyl)-thienyl, 3-(3'-trifluoromethyl)-thienyl, 3(3'-chloro)-thienyl, 3-(3'-methyl)-thienyl, 3-(3'-phenyl)thienyl, 3-(2'-(3-trifluoromethyl-phenyl))-thienyl, 3-(2'-(4-methoxyphenyl))thienyl, 3-(2'-methyl)-thienyl, 5-trifluoromethyl-3-benzo[b]thienyl, 3-cyclopentano[b]thienyl, 2-cyclopentano[b]thienyl, and 2-cyclohexano[b]thienyl.

The following compounds are, for example, mentioned as especially suitable for this invention:

9α,11α,15-trihydroxy-16-(3-thienyloxy)-5-cis,13-trans-tetranor-prostadienic acid, 9α,11α,15-trihydroxy-16-methyl-16-(3-thienyloxy)-5-cis,13-trans-tetranor-prostadienic acid, 9α,11α,15-trihydroxy-16,16-dimethyl-16-(3-thienyloxy)-5-cis, 13-tetranor-prostadienic acid, 9α,11α,15-trihydroxy-16-(2-(2'-methyl)-thienyloxy)-5-cis,13-trans-tetranor-prostadienic acid, 9α,11α,15-trihydroxy-16,16-dimethyl-16-(2-(2'-methyl)-thienyloxy)-5-cis,13-trans-tetranor-prostadienic acid, 9α,11α,15-trihydroxy-16-(2-(3-methoxy)-thienyloxy)-5-cis,13-trans-tetranor-prostadienic acid, 9α,11α,15-trihydroxy-16-(2-(3-methoxy)-thienylmethyloxy)-5- cis,13-trans-tetranor-prostadienic acid, 9α,11α,15-trihydroxy-16-(3-(2-ethoxymethyl)-thienyloxy)-5-cis,13-trans-tetranor-prostadienic acid, 9α,11α,15-trihydroxy-16-(3-(2-methoxymethyl)-thienyloxy)-5-cis,13-trans-tetranor-prostadienic acid, 9α,11α,15-trihydroxy-17-(2-(3-chloro)-thienyloxy)-5-cis,13-trans-trinor-prostadienic acid, 9α,11α,15-trihydroxy-16-(2-(2-thienyloxy)-ethoxy)-5-cis,13-trans-tetranor-prostadienic acid, 9α,11α,15-trihydroxy-16-(3-(2',3'-dimethyl)-thienyloxy)-5-cis,13-trans-tetranor-prostadienic acid, 9α,11α,15-trihydroxy-16-(3-(3'-trifluoromethyl)-thienyloxy)-5-cis,13-trans-tetranor-prostadienic acid, 9α,11α,15-trihydroxy-16-(3-(3'-chloro)-thienyloxy)-5-cis,13-trans-tetranor-prostadienic acid, 9α,11α,15-trihydroxy-16-ethyl-16-(3-(3'-methyl)-thienyloxy)-5-cis,13-trans-tetranor-prostadienic acid, 9α,11α,15-trihydroxy-16-(3-(3'-phenyl)-thienyloxy)-5-cis,13-trans-tetranor-prostadienic acid, 9α,11α,15-trihydroxy-16-(3-(2'-(3"chlorophenyl))-thienyloxy)-5-cis,13-trans-tetranor-prostadienic acid, 9α,11α,15-trihydroxy-16-(3-(2'-(3"-trifluoromethylphenyl))-thienyloxy)-5-cis,13-trans-tetranor-prostadienic acid, 9α,11α,15-trihydroxy-16-(3-(2'-(4"-methoxyphenyl))-thienyloxy)-5-cis,13-trans-tetranor-prostadienic acid, 9α,11α,15-trihydroxy-16-(3-(2'-methyl)-thienyloxy)-5-cis,13-trans-tetranor-prostadienic acid, 9α,11α,15-trihydroxy-16-(4-methoxy)-3-benzo[b]-thienyloxy)-5-cis-,13-trans-tetranor-prostadienic acid, 9α,11α,15-trihydroxy-16-(5-trifluoromethyl)-3-benzo[b]-thienyloxy)-5-cis,13-trans-tetranor-prostadienic acid, 9α,11α,15-trihydroxy-16-(5-chloro)-3-benzo[b]-thienyloxy)-5-cis,13-trans-tetranor-prostadienic acid, 9α,11α,15-trihydroxy-16-(3-cyclopentano[b]-thienyloxy)-5-cis,13-trans-tetranor-prostadienic acid, 9α,11α,15-trihydroxy-16-(2-cyclopentano[b]-thienyloxy)-5-cis,13-trans-tetranor-prostadienic acid, 9α,11α,15-trihydroxy-16-(2-cyclohexano[b]-thienyloxy)-5-cis,13-trans-tetranor-prostadienic acid, preferably the 9α,11α,15α-epimers thereof.

Among the compounds of formula I cited sub 2.4, there are suitable for this invention those in which X stands for the methylene, ethylene, trimethylene, ethylidene, isopropylidene, or trimethylene group, and R for the phenyl, benzyl, furfuryl, 1-naphthyl, 2-naphthyl, 2-, 3- and 4-chlorophenyl, 4-bromophenyl, 2-, 3- and 4-fluorophenyl, 2,3-, 2,4-, 2,5-, 2,6-, 3,4- and 3,5-dichlorophenyl, 2-, 3- and 4-tolyl, 2,3-, 3,4- and 3,5-xylyl, 4-tert.-butylphenyl, 3-allylphenyl, 3-trifluoromethylphenyl, 4-hydroxyphenyl, 2-, 3- and 4-methoxyphenyl, 4-biphenylyl, 3-dimethylaminophenyl, 2-chloro-4-methylphenyl, 1-chloro-2-naphthyl, 4-chloro-2-naphthyl, 6-methyl-2-naphthyl, 6-methoxy-2-naphthyl and 5,6,7,8-tetrahydro-2-naphthyl group.

The following compounds are especially mentioned to be suitable for this invention, for example:

9α,11α,15-trihydroxy-16-(4-fluorophenoxy)-17,18,19,20-tetranor-5-cis,13-trans-prostadienic acid, 9α,11α,15-trihydroxy-16-(3-chlorophenoxy)-17,18,19,20-tetranor-5-cis,13-trans-prostadienic acid, 9α,11α,15-trihydroxy-16-(3-trifluoromethylphenoxy)-17,18,19,20-tetranor-5-cis, 13-trans-prostadienic acid, preferably the corresponding 15α-epimers.

As compounds to be used according to the invention and selected from the group of the luteolytically effective prostaglandins, there are further mentioned compounds of the formula II

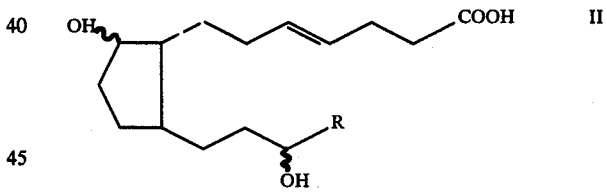

in which R stands for a saturated, straight chain or branched chain alkyl group of 1 to 20 carbon atoms, which may be substituted by an O-alkyl group of 1 to 5 carbon atoms, an O-aryl group, an O-furyl group or an O-benzyl group, which may also be substituted by one or more halogen atoms, trifluoromethyl or alkyl groups of 1 to 3 carbon atoms, or by a phenoxy group, which may carry one or more halogen atoms, or for a saturated cycloalkyl group of 3 to 7 ring members or for an aryl or furyl group, which may be substituted by one or more alkyl groups of 1 to 3 carbon atoms (see German Offenlegungsschrift No. 2,407, 186).

Preferred are those compounds in which R is defined as follows:

an alkyl group of 3 to 8 carbon atoms, a cycloalkyl group of 3 to 7 carbon atoms, a phenyl group which may be unsubstituted or substituted by one or more methyl groups; furthermore the radicals of the formula —C(R')$_2$—(CH$_2$)$_n$—O—R", wherein R' stands for hydrogen or an alkyl group of 1 to 3 carbon atoms, especially the methyl group, with the proviso that the two R' are identical or different, and n is 0 or 1, and R" stands for an alkyl group of 1 to 5 carbon atoms, a phenyl or benzyl group which may carry, on their nucleus, one or more halogen atoms, especially chlorine atoms, trifluoromethyl or alkyl groups of 1 to 3 carbon atoms, or for a diphenyl ether radical, wherein the terminal phenyl group may carry one or more halogen atoms, especially chlorine atoms, trifluoromethyl or alkyl groups of 1 to 3 carbon atoms; particularly preferred for R are the radicals of the formula —C(R')$_2$—(CH$_2$)$_n$—O—R"—, wherein n is 0 and R" stands for a phenyl group substituted by one chlorine atom or trifluoromethyl group or for a diphenyl ether radical, wherein the terminal phenyl group carries one chlorine atom.

The following compounds are especially mentioned to be useful for the combination of the invention:

7-[2-(3-Hydroxy-3-pentyl-trans-1-propenyl)-5-hydroxy--cyclopentyl]-cis--4-heptenoic acid:

7-[2-(hydroxy-3-heptyl-trans-1-propenyl)-5-hydroxy-cyclopentyl]-cis-4-heptenoic acid, 7-[2-(3-hydroxy-3-cyclohexyl-trans-1-propenyl)-5-hydroxy-cyclopentyl]-cis-4-heptenoic acid, 7-[2-[3-hydroxy-3-(1,1-dimethyl-3-oxa-pentyl)-trans-1-propenyl]-5-hydroxy-cyclopentyl]-cis-4-heptenoic acid, 7-[2-(3-hydroxy-3-cycloheptyl-trans-1-propenyl)-5-hydroxy-cyclopentyl]-cis-4-heptenoic acid, 7-[2-(3-hydroxy-trans-1-hexenyl)-5-hydroxy-cyclopentyl]-cis-4-heptenoic acid, 7-[2-[3-hydroxy-3-[1-methyl-[p(p-chlorophenoxy)-phenoxy]-methyl]-trans-1-propenyl]-5-hydroxy-cyclopentyl]-cis-4-heptenoic acid, 7-[2-[3-hydroxy-3-[1,1-dimethyl-1-[4-(4-chlorophenoxy)phenoxy]-methyl]-trans-1-propenyl]-5-hydroxy-cyclopentyl]-cis-4-heptenoic acid, 7-[2-(3-hydroxy-3-phenoxymethyl-trans-1-propenyl)-5-hydroxycyclopentyl]-cis-4-heptenoic acid, 7-[2-[3-hydroxy-3-(4-fluorophenoxy)-methyl-trans-1-propenyl]-5-hydroxy-cyclopentyl]-cis-4-heptenoic acid, 7-[2-[3-hydroxy-3-(3-chlorophenoxy)-methyl-trans-1-propenyl]-5-hydroxy-cyclopentyl]-cis-4-heptenoic acid, 7-[2-[3-hydroxy-3-(3-trifluoromethylphenoxy)-methyl-trans-1-propenyl]-5-hydroxy-cyclopentyl]-cis-4-heptenoic acid, 7-[2-[3-hydroxy-3-(1,1-dimethylpentyl)-trans-1-propenyl]-5-hydroxy-cyclopentyl]-cis-4-heptenoic acid, and 7-[2-[3-hydroxy-3-isobutyl-trans-1-propenyl]-5-hydroxy-cyclopentyl]-cis-4-heptenoic acid.

Useful compounds of this invention are also the esters of the above-mentioned prostadienic acids with aliphatic alcohols of 1 to 5 carbon atoms, cycloaliphatic alcohols of 3 to 8 carbon atoms and araliphatic alcohols of 7 or 8 carbon atoms, as well as the physiologically acceptable amine or metal salts thereof, for example methyl, ethyl, propyl, isopropyl, n- and isobutyl, pentyl, benzyl esters, and alkali metal salts, benzylammonium, triethylammonium and morpholine salts.

Useful compounds for this invention selected from the group of the estrogenic compounds are, above all, the natural steroidal estrogens, for example estrone, estradiol and estriol, especially estradiol, and the esters thereof, for example estradiol-3-benzoate, estradiol-17β-propionate, estradiol-17β-valeriate and estradiol-17β-(β-cyclopentyl)-propionate; semisynthetic steroidal estrogens, for example 17α-ethynyl-estradiol and the 3-ethers thereof, such as the 3-methyl- and 3-cyclopentyl ethers, and non-steroidal estrogenic substances, for example diethyl stilbestrol, hexestrol and dienestrol and the esters thereof, for example diethyl stilbestrol dipropionate, dipalmiate and diphosphoric acid ester, and the ethers thereof, for example diethyl stilbestrol methyl and dimethyl ethers.

In the combination of the invention of the active substances selected from the group of the luteolytically effective compounds, on the one hand, and of the estrogenous compounds, on the other hand, which may be both administered by the oral and especially by the parenteral routes, the weight ratio of the active substances may range from about 1:1 to 1:5,000, preferably from 1:20 to 1:100.

The experimental results hereinafter given on the luteolytic effect of the separate active substances as well as of the combination thereof demonstrate the synergistic effect of the combination of the invention.

The amounts of active substances indicated have been administered to grown-up cattle within a period of from the fifth to the 20th day of the estrus cycle by the intravenous, intramuscular or subcutaneous route. When the luteolytic activity was high enough, estrus was induced 2 to 4 days after administration. The efficacy of the preparations was additionally tested by monitoring the course of progesterone concentration.

COMBINATION EFFECT (LUTEOLYSIS) OF 17β-ESTRADIOL (17β-E$_2$) AND LUTEOLYTIC PROSTAGLANDINS IN CATTLE (INTRAVENOUS)

TABLE 1

| 9 α,11α,15 α-trihydroxy-16(3-trifluoromethylphenoxy)-17,18,19 20-tetranor-5-cis,13-trans-prostadienic acid (A) | | |
|---|---|---|
| A μg | 17β-E$_2$ mg | luteolytic effect |
| 1000 | — | + |
| 750 | — | + |
| 500 | — | +/− |
| 250 | — | — |
| 200 | 6 | + |
| 100 | 6 | + |
| 50 | 6 | + |
| 10 | 50 | (+) |
| — | 6 | — |
| — | 10 | — |
| — | 50 | — |

TABLE 2

| 9 α,11α,15α-trihydroxy-(16-(3-thienyloxy)-5-cis,3-trans-tetranor-prostadienic acid (B) | | |
|---|---|---|
| B μg | 17β-E$_2$ mg | luteolytic effect |
| 1000 | — | + |
| 500 | — | — |
| 340 | 6 | + |
| — | 6 | — |
| — | 10 | — |
| — | 50 | — |

TABLE 3

| Prostaglandin F$_2$α: (PG F$_2$α) | | |
|---|---|---|
| PG F$_2$α | 17β-E$_2$ | luteolytic effect |
| 50 mg | — | + |
| 20 mg | — | — |
| 5 mg | — | — |
| 5 mg | 6 mg | + |
| — | 6 mg | — |
| — | 10 mg | — |

TABLE 3-continued

| Prostaglandin F₂α: (PG F₂α) | | |
|---|---|---|
| PG F₂α | 17β-E₂ | luteolytic effect |
| — | 50 mg | — |

TABLE 4

| 7-[2-[3-hydroxy-3-(4-fluorophenoxy)-methyl-trans-1-propenyl]-5-hydroxy-cyclopentyl]-cis-4-heptenoic acid (C) | | |
|---|---|---|
| C | 17β-E₂ | luteolytic effect |
| 10 mg | — | + |
| 5 mg | 6 mg | + |

TABLE 5

| 7-[2-[3-hydroxy-3-phenoxymethyl-trans-1-propenyl]-5-hydroxy-cyclopentyl]-cis-4-heptenoic acid (D) | | |
|---|---|---|
| D | 17β-E₂ | luetolytic effect |
| 10 mg | — | + |
| 5 mg | 6 mg | + |

As is evident from the experimental data given in the Tables, the combined active substances of the invention are suitable for controlling the estrus cycle in animals. In this connection, it is important to know that, in comparison with the prostaglandins used alone, substantially lower amounts of prostaglandin are required to induce estrus. It should further be stressed that estrus is induced by a single injection; hence permanent administration or depot preparations are not necessary. The active substances may also be administered separately. The active substances of the invention may also be used for inducing labor, especially in women. For this purpose, they may be administered, for example, in the form of a sterile aqueous solution by injection or intravenous infusion until labor commences. In this case, the combined active substances of the invention may also be administered together with a substance that has a stimulating effect on the uterus, for example oxytocin.

The combined active substances of the invention may be administered in the usual dosage unit forms, such as tablets, powders, capsules, dragees, suppositories, solutions, suspensions or in the form of depot preparations. A preferred dosage unit form is an injection solution for an intravenous, intramuscular or subcutaneous injection.

The pharmaceutically active preparations may be combined with the usual pharmaceutical adjuvants, for example inert diluents, such as lactose; disintegrating agents, for example corn starch; lubricants, for example talc, and/or agents for achieving a depot effect, for example cellulose acetate phthalate or polyvinyl acetate.

As solvents to be used for injections, there may be used, for example, water, physiological sodium chloride solutions, alcohols, such as ethanol, propane-diol, glycerol or polyethylene glycol; olive oil or sugar solutions, for example glucose or mannitol solutions.

The following Examples illustrate the invention:

EXAMPLE 1

0.35 Milligram of 9α,11α,15α-trihydroxy-16-(3-thienyloxy)-5-cis,13-trans-tetranor-prostadienic acid was mixed with 6 mg of 17β-estradiol benzoate, and the mixture was dissolved with absolute ethanol to yield 10 ml of an injection solution ready for use.

EXAMPLE 2

The same compounds as mentioned in Example 1 were mixed in the same ratio and dissolved in oleum olivarium to yield 10 ml of an injection solution ready for use.

EXAMPLE 3

0.1 Milligram of Fluprostenol (9α,11α,15α-trihydroxy-16-(3-trifluoromethylphenoxy)-5-cis,13-trans-tetranor-prostadienic acid) was mixed with 6 mg of 17β-estradiol, and the mixture was dissolved in absolute ethanol to yield 10 ml of an injection solution ready for use.

What is claimed is:

1. A leutolytically-active pharmaceutical composition comprising an injectable or orally-administrable carrier and, as the active ingredient, a combination of at least one luteolytically effective prostaglandin or a physiologically acceptable salt or ester thereof and at least one estrogen or an ester or ether thereof in a weight ratio from 1:1 to 1:5000.

2. A pharmaceutical composition as in claim 1 wherein the luteolytically effective ingredient is a 9α,11α,15-trihydroxy-5-cis,13-trans-prostadienic acid or a physiologically acceptable salt or ester thereof.

3. A pharmaceutical composition as in claim 1 wherein the luteolytically effective ingredient is a homolog of a 9α,11α,15-trihydroxy-5-cis,13-trans-prostadienic acid, said homolog having a side chain containing from 4 to 10 unsubstituted or substituted carbon atoms in the side chain in the 12-position.

4. A pharmaceutical composition as in claim 1 wherein the luteolytically effective ingredient is a 17-oxaor 18-oxa- derivative of a 9α,11α,15-trihydroxy-5-cis,13-transprostadienic acid.

5. A pharmaceutical composition as in claim 1 wherein said estrogen is a natural or semisynthetic steroidal estrogen.

6. A pharmaceutical composition as in claim 1 wherein said estrogen is a non-steroidal estrogen.

7. A pharmaceutical composition as in claim 1 which additionally comprises a gonadotropin or an agent having a stimulating effect on the uterus.

8. A method for synchronizing estrus in a commercially-reared animal which comprises orally or parenterally administering to said animal, between the 5th day and 20th day of the estrus cycle, a luteolytically effective amount of the pharmaceutical composition of claim 1.

* * * * *